United States Patent
Muratore et al.

(10) Patent No.: US 10,723,971 B2
(45) Date of Patent: Jul. 28, 2020

(54) ACETALS OF 1-(3,3-DIMETHYLCYCLOHEX-1-ENYL) ETHANONE, METHOD FOR THE PRODUCTION THEREOF AND USE OF SAME IN PERFUMERY

(71) Applicant: V. MANE FILS, Le Bar sur Loup (FR)

(72) Inventors: Agnès Muratore, Châteauneuf (FR); Cyril Mahaim, Le Mont-sur-Lausanne (CH)

(73) Assignee: V. MANE FILS, Le Bar sur Loup (FR)

( * ) Notice: Subject to any disclaimer, the term of this patent is extended or adjusted under 35 U.S.C. 154(b) by 0 days.

(21) Appl. No.: 15/537,165

(22) PCT Filed: Dec. 14, 2015

(86) PCT No.: PCT/FR2015/053495
§ 371 (c)(1),
(2) Date: Jun. 16, 2017

(87) PCT Pub. No.: WO2016/097569
PCT Pub. Date: Jun. 23, 2016

(65) Prior Publication Data
US 2017/0342343 A1 Nov. 30, 2017

(30) Foreign Application Priority Data
Dec. 18, 2014 (FR) .................................. 14 62834

(51) Int. Cl.
| | | |
|---|---|---|
| *C11B 9/00* | (2006.01) | |
| *C07D 317/12* | (2006.01) | |
| *C07D 321/06* | (2006.01) | |
| *A61Q 13/00* | (2006.01) | |
| *C07D 319/06* | (2006.01) | |
| *A61K 8/49* | (2006.01) | |

(52) U.S. Cl.
CPC .......... *C11B 9/0076* (2013.01); *A61K 8/4973* (2013.01); *A61Q 13/00* (2013.01); *C07D 317/12* (2013.01); *C07D 319/06* (2013.01); *C07D 321/06* (2013.01); *C11B 9/0084* (2013.01)

(58) Field of Classification Search
CPC .................................................. A61K 8/4973
See application file for complete search history.

(56) References Cited

U.S. PATENT DOCUMENTS

| | | | |
|---|---|---|---|
| 3,144,465 A | 8/1964 | Ruzicka | |
| 4,163,866 A | 8/1979 | Strickler | |
| 4,264,467 A | 4/1981 | Schulte-Elte et al. | |
| 4,289,659 A * | 9/1981 | Schulte-Elte | ........... C07C 29/32 510/104 |
| 5,166,412 A | 11/1992 | Giersch et al. | |
| 6,348,618 B1 | 2/2002 | Anderson et al. | |
| 7,468,447 B1 | 12/2008 | Boden et al. | |

FOREIGN PATENT DOCUMENTS

| | | |
|---|---|---|
| EP | 0276998 | 8/1988 |
| FR | 2259091 | 8/1975 |

OTHER PUBLICATIONS

International Search Report for PCT/FR2015/053495, dated Mar. 9, 2016.
Written Opinion of the International Searching Authority for PCT/FR2015/053495, dated Mar. 9, 2016.

* cited by examiner

*Primary Examiner* — Arrie L Reuther
(74) *Attorney, Agent, or Firm* — B. Aaron Schulman, Esq.; Stites & Harbison, PLLC

(57) ABSTRACT

The present invention concerns new fragrant compounds exhibiting animal or amber notes, without any woody aspect. More particularly, new acetal derivatives of 1-(3,3-dimethylcyclohex-1-enyl)ethanone are disclosed, which correspond to the following general formula I:

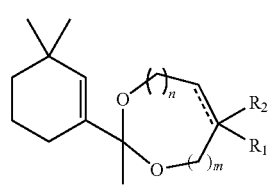

as well as a method of synthesising said compounds, and their use in perfumery.

17 Claims, No Drawings

ACETALS OF 1-(3,3-DIMETHYLCYCLOHEX-1-ENYL) ETHANONE, METHOD FOR THE PRODUCTION THEREOF AND USE OF SAME IN PERFUMERY

The object of the present invention is new acetals of 1-(3,3-dimethylcyclohex-1-enyl)ethanone possessing amber or animal notes, their preparation method, and also their uses in the chemicals industry, and in particular in perfumery, cosmetics, and in the detergents industry, said compounds exhibiting a particular fragrance and a particular persistence.

The perfume industry is always seeking new organoleptic compounds exhibiting an intense olfactory power while having the lowest possible production costs. More particularly, compounds displaying amber or animal notes are rare and difficult to obtain. Furthermore, obtaining compounds which have amber or animal notes whilst having no woody note, all at a low cost price, is becoming less and less easy.

Among the organoleptic molecules of interest in perfumery, compounds endowed with amber and/or animal notes are rare. Among the most commonly used can be numbered Ambrinol® (Firmenich, Switzerland) or 2,5,5-trimethyl-1,2,3,4,4a,5,6,7-octahydronaphthalen-2-ol (DE 2733928) or Grisalva® (IFF, USA) or 3a-ethyl-6,6,9a-trimethyldodecahydronaphtho[2,1-c]furan (U.S. Pat. No. 7,468,447), both represented below:

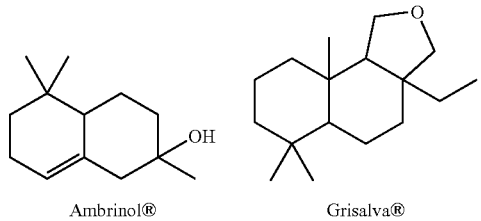 [SMILES: CC1(O)CCC2C(=CCCC2(C)C)C1 ; CCC12CCC3C(C)(C)CCCC3(C)C1COC2]

Ambrinol®  Grisalva®

Yet the main disadvantage of many compounds endowed with an amber and/or animal note is due to the complexity of their synthesis methods, which makes them very costly raw materials and difficult to obtain at high yield. For example, Ambrinol® can be prepared in two steps from β-ionone (U.S. Pat. No. 4,163,866); however, the first step of thermolysis, performed at between 300 and 500° C., leads to an intermediate product dehydroambrinol (precursor of ambrinol) at a level of only 27%. In addition, the second step of hydrogenation provides a mixture of α- and β-ambrinol isomers, whereas only the α-ambrinol isomer is desired. Similarly, the method of synthesising Grisalva® includes no fewer than nine steps from 1-(2,2,6,-trimethyl-cyclohexyl)-pentan-3-one (U.S. Pat. No. 7,468,447).

Also, in order to meet the constant needs of the perfume and flavour industry, the Applicant has identified new acetal derivatives of 1-(3,3-dimethylcyclohex-1-enyl)ethanone, these compounds exhibiting a very powerful and diffusive amber or animal note, as well as remarkable persistence.

These acetal derivatives of 1-(3,3-dimethylcyclohex-1-enyl)ethanone correspond to the following general formula I:

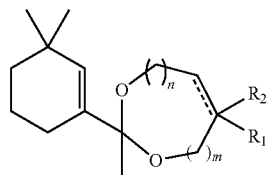

wherein:

m and n represent a carbon number (methylene group) and are each independently 0 or 1;

$R_1$ represents a hydrogen atom or a saturated $C_1$-$C_2$ alkyl group;

the carbon-carbon bond shown as a dotted line is present or absent, and when said bond is absent, $R_2$ is present and represents a hydrogen atom or a saturated $C_1$-$C_2$ alkyl group, when said bond is present, $R_2$ is absent;

said compound being in the form of a stereoisomer, a mixture of stereoisomers, or a racemic mixture.

According to a preferred embodiment, m and n represent a —$CH_2$— group number and are each independently 0 or 1.

The present invention also relates to a composition comprising at least one compound of general formula I.

Furthermore, a third object of the present invention relates to a method of preparing a compound of general formula I, said method being simple, efficient in terms of yield, including a small number of steps and therefore inexpensive.

Lastly, a final object of the present invention relates to the use of at least one compound of general formula I as a fragrant agent.

To the knowledge of the Applicant, none of the compounds corresponding to the general formula I has been previously identified.

Some acetal derivatives of 1-(3,3-dimethylcyclohexyl)ethanone were described in patent application EP 0472966, particularly 2-(3,3-dimethylcyclohexyl)-2,4-dimethyl-1,3-dioxolane and 2-(3,3-dimethylcyclohexyl)-2,4,4-trimethyl-1,3-dioxolane). However, said derivatives are described therein simply as intermediates of synthesis, and no olfactory description is associated with them.

In addition, the prior art describes other acetal compounds represented below, such as Karanal® (Givaudan, Switzerland) or 5-sec-butyl-2-(2,4-dimethylcyclohex-3-enyl)-5-methyl-1,3-dioxane (EP 0276998), Ysamber K® (Dragoco, Japan) or spiro[1,3-dioxolane-2,8'(5'h)-[2h-2,4a]methanonaphthalene] (EP 543470), or even Amberketal® (Firmenich, Switzerland) or dodecahydro-3,8,8,11a-tetramethyl-5h-3,5a-epoxynaphth[2,1-c]oxepine (U.S. Pat. No. 3,144,465).

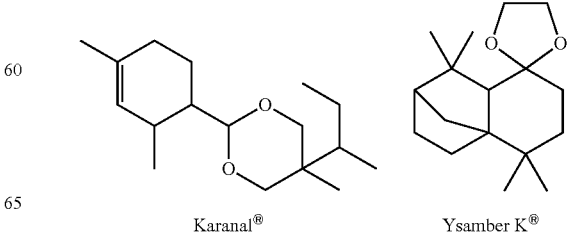

Karanal®  Ysamber K®

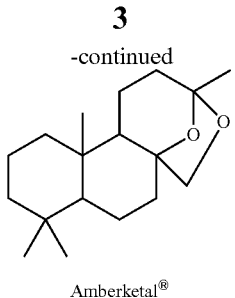

Amberketal®

However, these compounds possess on the one hand a chemical structure very different from that of the compounds of the present invention, and on the other hand amber notes associated with woody notes. Similarly, the ketones of formula I object of patent FR-B-2259091, such as the compound 1-(3,3-dimethylcyclohex-1-ene-1-yl)-1,1-ethylenedioxy-pent-4-ene), and some of their acetals, also possess a chemical structure very different from that of the compounds of the present invention and exhibit, here again, a woody note. On the contrary, the compounds according to the present invention have the advantage of exhibiting animal or amber notes free from a woody aspect.

Hence the object of the invention is a compound of the following general formula I:

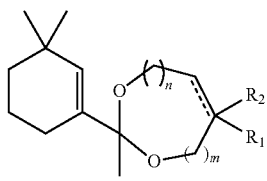

I wherein:
m and n represent a carbon number (methylene group) and are each independently 0 or 1;
$R_1$ represents a hydrogen atom or a saturated $C_1$-$C_2$ alkyl group;
the carbon-carbon bond shown as a dotted line is present or absent, and
when said bond is absent, $R_2$ is present and represents a hydrogen atom or a saturated $C_1$-$C_2$ alkyl group,
when said bond is present, $R_2$ is absent;
said compound being in the form of a stereoisomer, a mixture of stereoisomers, or a racemic mixture.

As indicated previously, according to a preferred embodiment, m and n represent a —$CH_2$— group number and are each independently 0 or 1.

Within the terms of the present invention, the term "$C_1$-$C_2$ alkyl" denotes any monovalent radical derived from a saturated linear carbon chain, containing 1 or 2 carbon atoms, i.e. a methyl or ethyl group.

According to a first embodiment, the carbon-carbon bond shown as a dotted line is absent. Preferably, n is equal to zero and m is equal to 1.

According to another preferred embodiment, n and m are equal to zero.

In a final embodiment, groups $R_1$ and $R_2$ represent a saturated $C_1$-$C_2$ alkyl group.

Even more preferably, the compound according to the present invention is chosen from 2-(3,3-dimethylcyclohex-1-enyl)-2-methyl-1,3-dioxolane, 2-(3,3-dimethylcyclohex-1-enyl)-2,4-dimethyl-1,3-dioxolane, 2-(3,3-dimethylcyclohex-1-enyl)-2-methyl-1,3-dioxane, 2-(3,3-dimethylcyclohex-1-enyl)-2,5-dimethyl-1,3-dioxane, 2-(3,3-dimethylcyclohex-1-enyl)-2,5,5-trimethyl-1,3-dioxane, 2-(3,3-dimethylcyclohex-1-enyl)-5,5-diethyl-2-methyl-1,3-dioxane and 2-(3,3-dimethylcyclohex-1-enyl)-2-methyl-4,7-dihydro-1,3-dioxepine.

The presence of centres of asymmetry in the structure of compounds of formula I according to the invention leads to the existence, for each of them, of several enantiomeric and/or diastereomeric forms. The invention also covers the compounds represented by the general formula I in the form of mixtures of enantiomers and/or diastereomers, in variable proportions, particularly racemic mixtures. The invention also comprises compounds of formula I in the form of a single enantiomer and/or diastereomer. Mixtures of enantiomers/diastereomers or pure forms may be obtained by synthesis from optically enriched or optically pure starting products, or by means of separation methods by crystallisation or chromatography.

A second object of the present invention relates to a composition comprising at least one compound of general formula I as defined above. By virtue of the pleasant odour that they release, the compounds of the invention find numerous applications in perfumery. The term "perfumery" is used herein in its general sense; it denotes not only traditional perfumery (alcohol-based or otherwise), but also other fields in which the odour of products is important. Thus reference may be made to perfumery compositions in the usual and traditional sense (such as perfuming bases and concentrates, perfumes, eaux de Cologne, eaux de toilette, indoor air fresheners, room fragrances, scented candles and similar products), to topical compositions, particularly cosmetics (such as face and/or body creams, talcum powders, hair oils, shampoos, hair lotions, bath salts and oils, shower and/or bath gels, toilet soaps, body antiperspirants and deodorants, shaving lotions and creams, soaps, toothpastes, mouthwashes, pomades, and similar products), as well as to cleaning products, particularly household products (such as detergents, washing powders, softeners, indoor air fresheners, room fragrances and similar products).

Thus, the invention extends to a perfume composition comprising at least one compound of the invention. In particular, this may be a traditional perfumery composition, a cosmetic composition, cleaning product, or even a so-called "intermediate composition", intended for use in preparing compositions or finished products (especially perfumes, cosmetic products, cleaning products).

Such a scented composition is generally prepared from a basic product, in which the compound(s) of the invention is (are) incorporated. The basic product will be easily determined by the man skilled in the art, depending on the envisaged composition and therefore on the envisaged use. The composition of these basic products and the nature of their usual components, such as solvent(s) and/or additive(s), are well known to the man skilled in the art.

The constituent compounds of these scented compositions, in particular the compounds of the invention, may be incorporated into or onto an inert support material. The support materials that can be employed are numerous and varied, for example polar solvents, oils, greases, finely divided solids, cyclodextrins, maltodextrins, gums, resins and any other support material known for such compositions (for example, soaps, candles, pomades, textiles, wipes, scented gels . . . ).

Preferably, a composition according to the present invention comprises at least one compound chosen from 2-(3,3-dimethylcyclohex-1-enyl)-2-methyl-1,3-dioxolane, 2-(3,3- dimethylcyclohex-1-enyl)-2,4-dimethyl-1,3-dioxolane, 2-(3,3-dimethylcyclohex-1-enyl)-2-methyl-1,3-dioxane, 2-(3,3-dimethylcyclohex-1-enyl)-2,5-dimethyl-1,3-dioxane, 2-(3,3-dimethylcyclohex-1-enyl)-2,5,5-trimethyl-1,3-dioxane, 2-(3,3-dimethylcyclohex-1-enyl)-5,5-diethyl-2-methyl-1,3-dioxane and 2-(3,3-dimethylcyclohex-1-enyl)-2-methyl-4,7-dihydro-1,3-dioxepine.

The effective quantity of the compounds of the invention to be incorporate into these compositions is dependent on the nature of said compositions, the desired odourising effect and the nature of any other odorous compounds present. It is easily determined by the man skilled in the art, and can vary within a very wide range, from 0.1 to 99%, in particular 0.1 to 50%, in particular 0.1 to 30 wt % of the total weight of the composition. The percentages above are expressed in total weight of the composition.

According to a final particular embodiment, the composition is characterised in that it further comprises at least one other fragrant agent/odorous substance. The fragrant agents/odorous substances which can be used in combination with the compounds of the present invention may be natural products such as extracts, essential oils, absolutes, resinoids, resins, concretes etc., but also synthesis products such as hydrocarbons, alcohols, aldehydes, ketones, ethers, acids, esters, acetals, nitriles etc., particularly saturated or unsaturated, aliphatic, heterocyclic or carbocyclic compounds. Such fragrant agents/odorous substances are mentioned for example in S. Arctander, "Perfume and Flavor Chemicals" (Montclair, N.J., 1969), or in "Common Fragrance and Flavor Materials", Wiley-VCH, Weinheim, 2006. Finally, several compounds of the present invention may also be used in combination in the same composition.

A third object of the present invention relates to a method of synthesising compounds of formula I, as defined above.

Said method is advantageous in that it allows the use of raw materials available in large quantities, the implementation of mild reaction conditions easily adaptable to existing production lines, as well as the supplanting of reagents likely to cause harm to health or the environment, with a view to industrial application.

The compounds of the present invention are obtained via a method comprising the following steps:
 a) cyclisation/rearrangement of dehydrolinalool by an acid, into 1-(3,3-dimethylcyclohex-1-enyl)ethanone and;
 b) acetalisation of 1-(3,3-dimethylcyclohex-1-enyl)ethanone by a diol to obtain a compound of formula I.

Dehydrolinalool (DE 1643710) is an easily accessible and inexpensive raw material, thus allowing simple manufacture compatible with the requirements of industry. Preferably, the cyclisation/rearrangement reaction of dehydrolinalool is performed by adding an acid chosen from phosphoric acid or methanesulfonic acid, and gives rise to 1-(3,3-dimethylcyclohex-1-enyl)ethanone.

Step b) of the method according to the invention is performed by adding a diol to the compound obtained in step a), namely, 1-(3,3-dimethylcyclohex-1-enyl)ethanone. Preferably, the diol is chosen from ethylene glycol, neopentyl glycol, 1,2-propanediol, 2,2-diethyl-1,3-propanediol, 2-methyl-1,3-propanediol, 1,3-propanediol, or even cis-2-butene-1,4-diol. This acetalisation step is performed in the presence of triethyl orthoformate and a small quantity of an acid which acts as a catalyst and has the advantage of being regenerated (hence a saving on the cost of the method). Small quantity is understood to be a quantity equal to 1% of the mass of 1-(3,3-dimethylcyclohex-1-enyl)ethanone introduced into the reaction medium. Para-toluene sulfonic acid is for example an acid usable for this step b).

Advantageously, it is possible to perform step b) of the method directly from dehydroherbac. In the usual manner, the name "dehydroherbac" denotes a mixture of the isomers 1-(3,3-dimethylcyclohex-1-enyl)ethanone and 1-(3,3-dimethylcylohex-6-enyl)ethanone (U.S. Pat. No. 4,264,467), the relative proportion between these 2 isomers being of little importance.

Pure forms of these isomers may be obtained from dehydroherbac by means of well-known separation methods, such as separation by crystallisation and/or chromatography. It is also possible to start from the dehydroherbac mixture; the reaction in this case will take place on the isomer 1-(3,3-dimethylcyclohex-1-enyl)ethanone only, with the isomer 1-(3,3-dimethylcyclohex-6-enyl)ethanone reacting only very weakly.

Thus the method according to the present invention exhibits the advantages of being performed without a solvent, but also without water through the use of triethyl orthoformate, being performed at ambient temperature in a few hours, and finally having a yield of between 70% and 80%.

Lastly, the final object of the invention is the use of at least one compound of formula I according to the invention as a fragrant agent or compound, as an odour masking agent or as an odour neutralisation agent. The term "fragrant", is used herein to refer to any organoleptic compound pleasantly stimulating the sense of smell. The term "masking agent" or "masking" is understood as reducing or eliminating the perception of a bad odour generated by one or more constituent molecules of a product.

Furthermore, said compound can be used alone or in combination with at least one other fragrant agent/one other odorous substance and/or at least one solvent and/or at least one additive. The additional fragrant/odourising agent(s), solvent(s) and additive(s) are known to the man skilled in the art, who will be able to choose the most appropriate one(s) depending on the effect sought.

A particular embodiment of the invention lies in using a compound of formula I to modify or reinforce the organoleptic properties of a substance, a composition or an article.

"Organoleptic properties" is understood as any property able to alter, improve or reinforce the organoleptic perception of a substance, composition, or item by a user. Thus, by way of a preferred example, the organoleptic agent according to the invention may consist in a perfuming agent able to confer, alter, improve or reinforce the olfactory perception of a substance, composition or item.

The following examples illustrate a particular manner of preparing the compounds of the invention, as well as the olfactory profile of each of the compounds exemplified. These examples are given only for illustrative purposes, and must not be understood as limiting the general scope of the invention.

EXAMPLE 1

Preparation of 2-(3,3-dimethylcyclohex-1-enyl)-2-methyl-1,3-dioxolane

In a flask, an equivalent of dehydrolinalool is placed in toluene. This solution is refluxed. Phosphoric acid (10% of the mass of dehydrolinalool) is then added slowly dropwise. After 20 hours of agitation under reflux, and once returned to ambient temperature, the reaction medium is poured onto a saturated aqueous solution of sodium bicarbonate. The phases are separated. The organic phase is washed in water until neutral. After drying on magnesium sulphate, filtration and evaporation of the solvent, the crude product is distilled under reduced pressure: its boiling point is 52° C. at 53.3 Pascal.

The 1-(3,3-dimethylcyclohex-1-enyl)ethanone thus obtained is placed in 4 equivalents of ethylene glycol and 2 equivalents of triethyl orthoformate. At ambient temperature, para-toluene sulfonic acid is added (1% of the mass of 1-(3,3-dimethylcyclohex-1-enyl)ethanone introduced). The reaction medium is left under agitation in these conditions for twenty hours, and then poured onto a saturated aqueous solution of sodium bicarbonate. This aqueous phase is extracted twice in cyclohexane. The combined organic phases are washed in water until neutral. After drying on magnesium sulphate, filtration and concentration, the crude product is distilled under reduced pressure: its boiling point is 46° C. at 53.3 Pascal.

Olfactory description: animal, amber, aromatic, terpenic.

The 2-(3,3-dimethylcyclohex-1-enyl)-2-methyl-1,3-dioxolane thus obtained exhibits the following spectral characteristics:

$^1$H-NMR (200 MHz, CDCl$_3$): δ (ppm) 0.94 (s, 6H), 1.34-1.37 (m, 2H), 1.41 (s, 3H), 1.57-1.61 (m, 2H), 1.91 (td, J=6.2 Hz, 1.6 Hz, 2H), 3.70-3.85 (m, 2H), 3.85-3.95 (m, 2H), 5.56 (s, 1H).

$^{13}$C-NMR (50 MHz, CDCl$_3$): δ (ppm) 19.85, 23.76, 23.96, 29.92, 31.34, 36.95, 64.18, 109.31, 132.60, 134.75.

MS [e/m (%)]: 196 (M+, 0.2), 181 (100), 109 (21), 87 (82), 73 (14), 43 (32).

IR (film, cm$^{-1}$): 859m, 946w, 1043s, 1110w, 1187m, 1209m, 1371w, 2933m.

EXAMPLE 2

Preparation of 2-(3,3-dimethylcyclohex-1-enyl)-2,4-dimethyl-1,3-dioxolane 2-(3,3-dimethylcyclohex-1-enyl)-2,4-dimethyl-1,3-dioxolane is prepared according to the protocol described in Example 1 using 1,2-propanediol instead of ethylene glycol. The crude product, made up of 2-(3,3-dimethylcyclohex-1-enyl)-2,4-dimethyl-1,3-dioxolane in the form of two diastereomers in proportions 62:38, is distilled under reduced pressure: its boiling point is 49° C. at 66.7 Pascal.

Olfactory description: animal, camphorated.

The 2-(3,3-dimethylcyclohex-1-enyl)-2,4-dimethyl-1,3-dioxolane thus obtained exhibits the following spectral characteristics:

Majority isomer (62%):

$^1$H-NMR (200 MHz, CDCl$_3$): δ (ppm) 0.93 (s, 6H), 1.25 (d, J=6.1 Hz, 3H), 1.33-1.38 (m, 2H), 1.42 (s, 3H), 1.59-1.61 (m, 2H), 1.88-1.95 (m, 2H), 3.37-3.42 (m, 1H), 3.86-3.90 (m, 1H), 4.02-4.08 (m, 1H), 5.55 (s, 1H).

$^{13}$C-NMR (50 MHz, CDCl$_3$): δ (ppm) 18.99, 19.87, 24.00, 24.71, 29.92, 29.96, 31.31, 36.98, 70.58, 71.48, 109.56, 132.28, 135.11.

MS [e/m (%)]: 210 (M+, 0.3), 195 (100), 137 (24), 109 (34), 101 (998), 93 (10), 91 (14), 81 (11), 79 (15), 76 (15), 67 (16), 43 (64), 41 (16).

Minority isomer (32%):

$^1$H-NMR (200 MHz, CDCl$_3$): δ (ppm) 0.94 (s, 6H), 1.22 (d, J=6.1 Hz, 3H), 1.33-1.38 (m, 2H), 1.39 (s, 3H), 1.59-1.61 (m, 2H), 1.88-1.95 (m, 2H), 3.28-3.33 (m, 1H), 4.00-4.04 (m, 1H), 4.18-4.25 (m, 1H), 5.60 (s, 1H).

$^{13}$C-NMR (50 MHz, CDCl$_3$): δ (ppm) 18.35, 19.83, 24.00, 24.24, 29.80, 29.87, 31.35, 36.98, 70.92, 72.40, 109.50, 132.54, 136.30.

MS [e/m (%)]: 210 (M+, 0.3), 195 (100), 137 (25), 109 (33), 101 (58), 91 (13), 81 (11), 79 (14), 76 (14), 66 (14), 43 (54), 41 (15).

IR (film, cm$^{-1}$): 866m, 937w, 953w, 1038s, 1085s, 1187s, 1210s, 1370m, 2930m.

EXAMPLE 3

Preparation of 2-(3,3-dimethylcyclohex-1-enyl)-2,5-dimethyl-1,3-dioxane 2-(3,3-dimethylcyclohex-1-enyl)-2,5-dimethyl-1,3-dioxane is prepared according to the protocol described in Example 1, using 2-methyl-1,3-propanediol instead of ethylene glycol. The crude product, made up of 2-(3,3-dimethylcyclohex-1-enyl)-2,5-dimethyl-1,3-dioxane, is distilled under reduced pressure: its boiling point is 46° C. at 26.7 Pascal.

Olfactory description: amber, green, red fruits.

The 2-(3,3-dimethylcyclohex-1-enyl)-2,5-dimethyl-1,3-dioxane thus obtained exhibits the following spectral characteristics:

$^1$H-NMR (200 MHz, CDCl$_3$): δ (ppm) 0.64 (d, J=6.7 Hz, 3H), 0.85-1.06 (m, 1H), 0.98 (s, 6H), 1.32 (s, 3H), 1.41-1.43 (m, 2H), 1.61-1.65 (m, 2H), 1.84 (t, J=6.7 Hz, 1H), 1.97-2.07 (m, 1H), 3.26-3.34 (m, 2H), 3.63-3.68 (m, 2H), 5.56 (s, 1H).

$^{13}$C-NMR (50 MHz, CDCl$_3$): δ (ppm) 12.60, 20.05, 24.52, 28.69, 28.87, 29.91, 31.82, 37.08, 67.41, 100.23, 132.70, 136.17.

MS [e/m (%)]: 224 (M+, 0.2), 209 (54), 137 (22), 121 (10), 115 (100), 109 (22), 93 (14), 91 (13), 79 (15), 77 (12), 67 (11), 55 (26), 43 (41), 41 (14).

IR (film, cm$^{-1}$): 860m, 1034m, 1052m, 1100m, 1121m, 1162s, 1181s, 1225m, 1368w, 1457w, 2862w, 2930m, 2952m.

EXAMPLE 4

Preparation of 2-(3,3-dimethylcyclohex-1-enyl)-2,5,5-trimethyl-1,3-dioxane 2-(3,3-dimethylcyclohex-1-enyl)-2,5,5-trimethyl-1,3-dioxane is prepared according to the protocol described in Example 1, using neopentyl glycol instead of ethylene glycol. The crude product, made up of 2-(3,3-dimethylcyclohex-1-enyl)-2,5,5-trimethyl-1,3-dioxane, is distilled under reduced pressure: its boiling point is 68° C. at 26.7 Pascal.

Olfactory description: amber, musky, red fruits.

The 2-(3,3-dimethylcyclohex-1-enyl)-2,5,5-trimethyl-1,3-dioxane thus obtained exhibits the following spectral characteristics:

$^1$H-NMR (200 MHz, CDCl$_3$): δ (ppm) 0.67 (s, 3H), 0.98 (s, 6H), 1.17 (s, 3H), 1.35 (s, 3H), 1.39-1.43 (m, 2H), 1.61-1.65 (m, 2H), 1.85 (t, J=6.1 Hz, 2H), 3.25-3.28 (m, 2H), 3.42-3.50 (m, 2H), 5.56 (s, 1H).

$^{13}$C-NMR (50 MHz, CDCl$_3$): δ (ppm) 20.05, 22.15, 22.70, 24.42, 28.07, 29.51, 29.94, 31.79, 37.09, 71.41, 100.29, 132.63, 135.89.

MS [e/m (%)]: 238 (M+, 0.4), 223 (45), 137 (20), 129 (100), 109 (24), 93 (15), 91 (14), 81 (12), 79 (14), 77 (12), 69 (28), 67 (14), 55 (13), 43 (57), 41 (24).

IR (film, cm$^{-1}$): 859m, 1013m, 1039m, 1083s, 1121m, 1174s, 1207w, 1239w, 1369w, 1470w, 2864w, 2951m.

EXAMPLE 5

Preparation of 2-(3,3-dimethylcyclohex-1-enyl)-5,5-diethyl-2-methyl-1,3-dioxane 2-(3,3-dimethylcyclohex-1-enyl)-5,5-diethyl-2-methyl-1,3-dioxane is prepared according to the protocol described in Example 1, using 2,2-diethyl-1,3-propanediol instead of ethylene glycol. The crude product, made up of 2-(3,3-dimethylcyclohex-1-enyl)-5,5-diethyl-2-methyl-1,3-dioxane, is distilled under reduced pressure: its boiling point is 78° C. at 40.0 Pascal.
Olfactory description: slightly animal.
The 2-(3,3-dimethylcyclohex-1-enyl)-5,5-diethyl-2-methyl-1,3-dioxane thus obtained exhibits the following spectral characteristics:
$^{1}$H-NMR (200 MHz, CDCl$_3$): δ (ppm) 0.72 (t, J=7.5 Hz, 3H), 0.72 (t, J=7.6 Hz, 3H), 0.98 (s, 6H), 0.98-1.05 (m, 1H), 1.26-1.32 (m, 1H), 1.32 (s, 3H), 1.32-1.42 (m, 2H), 1.58-1.73 (m, 4H), 1.82-1.87 (m, 2H), 3.36-3.45 (m, 4H), 5.56 (s, 1H).
$^{13}$C-NMR (50 MHz, CDCl$_3$): δ (ppm) 6.61, 7.50, 20.05, 22.58, 24.42, 24.48, 27.97, 29.93, 31.76, 34.22, 37.10, 68.38, 100.47, 132.79, 135.79.
MS [e/m (%)]: 208 (M+, 0.1), 134 (19), 133 (46), 132 (17), 121 (11), 119 (13), 110 (11), 109 (10), 108 (13), 107 (17), 97 (17), 96 (10), 95 (13), 93 (23), 92 (11), 91 (34), 81 (26), 80 (10), 79 (35), 77 (14), 67 (28), 57 (100), 55 (23), 53 (11), 41 (49), 39 (12).
IR (film, cm$^{-1}$): 838w, 1365m, 1459m, 1726s, 2715w, 2866m, 2928s, 2951s.

EXAMPLE 6

Preparation of 2-(3,3-dimethylcyclohex-1-enyl)-2-methyl-4,7-dihydro-1,3-dioxepine 2-(3,3-dimethylcyclohex-1-enyl)-2-methyl-4,7-dihydro-1,3-dioxepine is prepared according to the protocol described in Example 1, using cis-2-butene-1,4-diol instead of ethylene glycol. The crude product, made up of 2-(3,3-dimethylcyclohex-1-enyl)-2-methyl-4,7-dihydro-1,3-dioxepine, is distilled under reduced pressure: its boiling point is 75° C. at 53.3 Pascal.
Olfactory description: amber, spicy, nutmeg, incense.
The 2-(3,3-dimethylcyclohex-1-enyl)-2-methyl-4,7-dihydro-1,3-dioxepine thus obtained exhibits the following spectral characteristics:
$^{1}$H-NMR (200 MHz, CDCl$_3$): δ (ppm) 0.98 (s, 6H), 1.37-1.41 (m, 2H), 1.38 (s, 3H), 1.58-1.66 (m, 2H), 1.91-1.96 (m, 2H), 4.10-4.26 (m, 4H), 5.65 (t, J=1.1, 2H), 5.76 (s, 1H).
$^{13}$C-NMR (50 MHz, CDCl$_3$): δ (ppm) 19.98, 22.41, 24.44, 30.06, 31.55, 37.08, 61.49, 103.40, 129.63, 133.88, 134.33.
MS [e/m (%)]: 222 (M+, 0.1), 207 (15), 154 (33), 152 (22), 137 (58), 109 (62), 93 (14), 91 (14), 81 (18), 79 (16), 77 (14), 70 (10), 69 (13), 67 (27), 55 (14), 53 (13), 43 (100), 42 (19), 41 (38), 39 (29).
IR (film, cm$^{-1}$): 613m, 625m, 640m, 787m, 877m, 949m, 1049s, 1082s, 1117m, 1153s, 1200w, 1231m, 1280m, 1371m, 1451w, 2861w, 2930m.

EXAMPLE 7

Perfuming Composition Containing the Derivatives Obtained in Examples 1 and 4

To a rose chord made according to the following table (Chord A) are added 2-(3,3-dimethylcyclohex-1-enyl)-2,5,5-trimethyl-1,3-dioxane (Example 4, Chords B and C) and 2-(3,3-dimethylcyclohex-1-enyl)-2-methyl-1,3-dioxolane (Example 1, Chord D).

| Ingredients | Chord A | Chord B | Chord C | Chord D |
|---|---|---|---|---|
| CITRONELLOL 90% | 100 | 100 | 100 | 100 |
| ALPHA DAMASCONE 10% DPG | 20 | 20 | 20 | 20 |
| DIMETHYLBENZYLCARBINYL ACETATE | 35 | 35 | 35 | 35 |
| EUGENOL RECT. | 5 | 5 | 5 | 5 |
| GERANIOL 95% | 150 | 150 | 150 | 150 |
| GERANYL ACETATE | 50 | 50 | 50 | 50 |
| CIS-3-HEXENOL | 30 | 30 | 30 | 30 |
| NEROL 90% | 25 | 25 | 25 | 25 |
| ROSE OXIDE | 10 | 10 | 10 | 10 |
| PHENYLETHYL PHENYLACETATE | 50 | 50 | 50 | 50 |
| PHENYLETHYL ALCOHOL | 400 | 400 | 400 | 400 |
| 2-(3,3-DIMETHYLCYCLOHEX-1-ENYL)-2,5,5-TRIMETHYL-1,3-DIOXANE (Example 4) | — | 25 | 50 | — |
| 2-(3,3-DIMETHYLCYCLOHEX-1-ENYL)-2-METHYL-1,3-DIOXOLANE (Example 1) | — | — | — | 25 |
| DIPROPYLENE GLYCOL—DPG | 125 | 100 | 75 | 100 |

Generally, the addition of the molecules boosts the chord, making it more powerful.
The addition of 2-(3,3-dimethylcyclohex-1-enyl)-2-methyl-1,3-dioxolane (Example 1, Chord D) gives an aromatic, camphorated effect (the rose is less opulent) whereas the addition of the derivative 2-(3,3-dimethylcyclohex-1-enyl)-2,5,5-trimethyl-1,3-dioxane (Example 4, Chords B and C) reinforces the rose note, giving it a lovely natural effect . . . .
Finally, Chords B and C are more spicy, cinnamic, sweet. Chord C is however more dry woody/amber, the note is less rosy than with Chord B (less balanced), but the dry woody effect fits the composition well, lending power and a floral woody note, with a very pleasant balmy effect.

EXAMPLE 8

Perfuming Composition Containing the Derivatives Obtained in Examples 1 and 4

To an apple chord made according to the following table (Chord A) are added 2-(3,3-dimethylcyclohex-1-enyl)-2,5,5-trimethyl-1,3-dioxane (Example 4, Chords B and C) and 2-(3,3-dimethylcyclohex-1-enyl)-2-methyl-1,3-dioxolane (Example 1, Chord D).

| Ingredients | Chord A | Chord B | Chord C | Chord D |
|---|---|---|---|---|
| GAMMA UNDECALACTONE | 100 | 100 | 100 | 100 |
| AMYL ISOBUTYRATE | 7 | 7 | 7 | 7 |
| GALAXOLIDE ™ 50% MIP | 225 | 225 | 225 | 225 |
| ISOAMYL ACETATE | 22 | 22 | 22 | 22 |
| STYRALLYL ACETATE | 8 | 8 | 8 | 8 |
| TRIPLAL ™ | 8 | 8 | 8 | 8 |

-continued

| Ingredients | Chord A | Chord B | Chord C | Chord D |
|---|---|---|---|---|
| 2-t-BUTYL-CYCLOHEXYL ACETATE 50% DPG | 523 | 523 | 523 | 523 |
| ETHYL METHYLVALERATE | 22 | 22 | 22 | 22 |
| VERTENOL ACETATE | 30 | 30 | 30 | 30 |
| 2-(3,3-DIMETHYLCYCLOHEX-1-ENYL)-2,5,5-TRIMETHYL-1,3-DIOXANE (Example 4) | — | 25 | 50 | — |
| 2-(3,3-DIMETHYLCYCLOHEX-1-ENYL)-2-METHYL-1,3-DIOXOLANE (Example 1) | — | — | — | 25 |
| DIPROPYLENE GLYCOL—DPG | 55 | 30 | 5 | 30 |

Generally, the addition of the molecules boosts the chord, making it more powerful and more natural.

The addition of 2-(3,3-dimethylcyclohex-1-enyl)-2-methyl-1,3-dioxolane (Example 1, Chord D) gives a natural apple, with a peel, acidulous effect.

The addition of the derivative 2-(3,3-dimethylcyclohex-1-enyl)-2,5,5-trimethyl-1,3-dioxane (Example 4, Chords B and C) gives a juicy, sugary, crisp effect.

EXAMPLE 9

Perfuming Composition Containing the Derivative Obtained in Example 4

To a woody chord made according to the following table (Chord A) is added 2-(3,3-dimethylcyclohex-1-enyl)-2,5,5-trimethyl-1,3-dioxane (Example 4, Chord B).

| Ingredients | Chord A | Chord B |
|---|---|---|
| ORCANOX ™ | 8 | 8 |
| PENTADECENOLIDE | 125 | 125 |
| HELIOTROPINE CRIST. 10% DPG | 6 | 6 |
| SANDELA ™ | 200 | 200 |
| METHYL DIHYDRO JASMONATE | 100 | 100 |
| MANDARIN ESS. DIST. COLOURLESS | 50 | 50 |
| IONONE ALPHA | 70 | 70 |
| DEHYDRO 2 CAMPHOLENYL PENTANOL | 4 | 4 |
| DEHYDRO CAMPHOLENYL BUTANOL | 110 | 110 |
| OCTAHYDRO-TETRAMETHYL ACETONAPHTONE | 250 | 250 |
| PERFUMERY VANILLIN | 10 | 10 |
| DIPROPYLENE GLYCOL—DPG | 67 | 42 |
| 2-(3,3-DIMETHYLCYCLOHEX-1-ENYL)-2,5,5-TRIMETHYL-1,3-DIOXANE (Example 4) | — | 25 |

Chord B, powdery, is a little less vanilla, more woody and masculine.

The invention claimed is:

1. A compound of the following general formula I:

wherein:
m and n represent a carbon number and are each independently 0 or 1;
$R_1$ represents a hydrogen atom or a saturated $C_1$-$C_2$ alkyl group;
the carbon-carbon bond shown as a dotted line is present or absent, and
when said bond is absent, $R_2$ is present and represents a hydrogen atom or a saturated $C_1$-$C_2$ alkyl group,
when said bond is present, $R_2$ is absent;
said compound being in the form of a stereoisomer, a mixture of stereoisomers, or a racemic mixture,
wherein said compound provides animal or amber fragrance notes without woody fragrance notes.

2. The compound according to claim 1, wherein said carbon-carbon bond shown as a dotted line is absent.

3. The compound according to claim 1, wherein n is 0 and m is 1.

4. The compound according to claim 1, wherein n and m are 0.

5. The compound according to claim 1, wherein $R_1$ and $R_2$ represent a saturated $C_1$-$C_2$ alkyl group.

6. The compound according to claim 1, said compound being selected from the group consisting of 2-(3,3-dimethylcyclohex-1-enyl)-2-methyl-1,3-dioxolane, 2-(3,3-dimethylcyclohex-1-enyl)-2,4-dimethyl-1,3-dioxolane, 2-(3,3-dimethylcyclohex-1-enyl)-2-methyl-1,3-dioxane, 2-(3,3-dimethylcyclohex-1-enyl)-2,5-dimethyl-1,3-dioxane, 2-(3,3-dimethylcyclohex-1-enyl)-2,5,5-trimethyl-1,3-dioxane, 2-(3,3-dimethylcyclohex-1-enyl)-5,5-diethyl-2-methyl-1,3-dioxane and 2-(3,3-dimethylcyclohex-1-enyl)-2-methyl-4,7-dihydro-1,3-dioxepine.

7. A composition comprising at least one compound according to claim 1, and
an inert support material.

8. The composition according to claim 7, said composition comprising at least one compound selected from the group consisting of 2-(3,3-dimethylcyclohex-1-enyl)-2-methyl-1,3-dioxolane, 2-(3,3-dimethylcyclohex-1-enyl)-2,4-dimethyl-1,3-dioxolane, 2-(3,3-dimethylcyclohex-1-enyl)-2-methyl-1,3-dioxane, 2-(3,3-dimethylcyclohex-1-enyl)-2,5-dimethyl-1,3-dioxane, 2-(3,3-dimethylcyclohex-1-enyl)-2,5,5-trimethyl-1,3-dioxane, 2-(3,3-dimethylcyclohex-1-enyl)-5,5-diethyl-2-methyl-1,3-dioxane and 2-(3,3-dimethylcyclohex-1-enyl)-2-methyl-4,7-dihydro-1,3-dioxepine.

9. The composition according to claim 7, wherein said compound is a fragrant agent; said composition further comprising at least one other fragrant agent.

10. The composition according to claim 7, wherein the compound of general formula I is present in a concentration of between 0.01 and 99 wt % of the total weight of the composition.

11. The composition according to claim 7, said composition being a perfume composition.

12. The composition according to claim 7, wherein said compound of general formula I is used in combination with at least one other fragrant agent and/or at least one solvent and/or at least one additive.

13. The composition according to claim 7, wherein the compound of general formula I is present in a concentration of between 0.1 and 30 wt % of the total weight of the composition.

14. The composition according to claim 7, wherein the inert support material is selected from the group consisting of polar solvents, oils, greases, finely divided solids, cyclodextrins, maltodextrins, gums, resins, soaps, candles, pomades, textiles, wipes, and scented gels.

15. A method of preparing a compound of general formula I according to claim 1, said method comprising:
   a) cyclisation/rearrangement of dehydrolinalool by an acid into 1-(3,3-dimethylcyclohex-1-enyl)ethanone, and;
   b) acetalisation of 1-(3,3-dimethylcyclohex-1-enyl)ethanone by a diol to obtain the compound of general formula I.

16. The method according to claim 15, wherein the acid in a) is chosen from phosphoric acid and methanesulfonic acid.

17. The method according to claim 15, wherein the diol in b) is chosen from ethylene glycol, neopentyl glycol, 1,2-propanediol, 2,2-diethyl-1,3-propanediol, 2-methyl-1,3-propanediol, 1,3-propanediol, or cis-2-butene-1,4-diol.

* * * * *